(12) United States Patent
Dewis et al.

(10) Patent No.: US 6,884,906 B2
(45) Date of Patent: Apr. 26, 2005

(54) MENTHYL HALF ACID ESTER DERIVATIVES, PROCESSES FOR PREPARING SAME, AND USES THEREOF FOR THEIR COOLING/REFRESHING EFFECT IN CONSUMABLE MATERIALS

(75) Inventors: Mark L. Dewis, Matawan, NJ (US); Michelle E. Huber, River Vale, NJ (US); Michael V. Cossette, Plainsboro, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 10/611,025

(22) Filed: Jul. 1, 2003

(65) Prior Publication Data

US 2005/0004214 A1 Jan. 6, 2005

(51) Int. Cl.$^7$ .......................... C07C 69/66; C07C 69/76; C07C 239/00; A61K 31/74; A61K 6/00
(52) U.S. Cl. .................... 560/188; 424/78.03; 424/401; 560/84; 560/106; 564/123
(58) Field of Search .......................... 560/84, 106, 115; 564/123; 424/78.03, 401

(56) References Cited

U.S. PATENT DOCUMENTS

| | | | |
|---|---|---|---|
| 3,111,127 A | 11/1963 | Jarboe ......................... | 131/276 |
| 4,029,759 A | 6/1977 | Humbert et al. .............. | 424/49 |
| 4,032,661 A | 6/1977 | Rowsell et al. ............. | 514/708 |
| 4,150,052 A | 4/1979 | Watson et al. ............... | 564/123 |
| 4,153,679 A | 5/1979 | Rowsell et al. ............... | 424/45 |
| 4,185,106 A | 1/1980 | Dittmar et al. ............. | 514/336 |
| 4,226,988 A | 10/1980 | Watson et al. .............. | 544/176 |
| 4,296,093 A | 10/1981 | Rowsell et al. ............... | 424/45 |
| 4,470,982 A | 9/1984 | Winkler ....................... | 514/188 |
| 4,472,421 A | 9/1984 | Buchel et al. .............. | 514/399 |
| 5,009,893 A | 4/1991 | Cherukuri et al. .......... | 424/440 |
| 5,545,424 A | 8/1996 | Nakatsu et al. ............. | 426/536 |
| 5,624,666 A | 4/1997 | Coffindaffer et al. .... | 424/70.21 |
| 5,641,480 A | 6/1997 | Vermeer ................... | 424/70.24 |
| 5,725,865 A | 3/1998 | Mane et al. ................ | 424/401 |
| 5,730,965 A | 3/1998 | Rapaport ................... | 424/70.1 |
| 5,843,466 A | 12/1998 | Mane et al. ................ | 424/401 |
| 5,955,066 A | 9/1999 | Sako et al. ............... | 424/70.12 |
| 6,110,520 A | 8/2000 | He et al. ..................... | 426/536 |
| 6,200,554 B1 | 3/2001 | Yeoh et al. ............... | 424/70.12 |
| 6,210,695 B1 | 4/2001 | Beerse et al. ............... | 424/404 |
| 6,248,315 B1 | 6/2001 | Young et al. ............ | 424/70.11 |
| 6,251,463 B1 | 6/2001 | Rossy et al. ................ | 426/533 |
| 6,294,186 B1 | 9/2001 | Beerse et al. ............... | 424/405 |
| 6,297,203 B1 | 10/2001 | Guskey et al. ............. | 510/124 |
| 6,299,900 B1 | 10/2001 | Reed et al. ................. | 424/449 |
| 6,303,817 B1 | 10/2001 | Boden et al. ............... | 564/129 |
| 6,328,982 B1 | 12/2001 | Shiroyama et al. ......... | 424/401 |
| 6,333,180 B1 | 12/2001 | Farbood et al. ............. | 435/148 |
| 6,338,855 B1 | 1/2002 | Albacarys et al. .......... | 424/401 |
| 6,365,215 B1 | 4/2002 | Grainger et al. ............ | 426/535 |
| 6,391,886 B1 | 5/2002 | Lee ............................ | 514/289 |
| 6,451,844 B1 | 9/2002 | Watkins et al. ............. | 514/423 |
| 6,455,080 B1 | 9/2002 | Wolf et al. ..................... | 426/3 |
| 6,572,914 B1 | 6/2003 | Borlinghaus ................ | 426/590 |
| 6,579,513 B1 | 6/2003 | Tashjian et al. ............. | 424/54 |
| 6,579,514 B1 | 6/2003 | Hall et al. ..................... | 426/54 |
| 6,579,516 B1 | 6/2003 | Mansouri ................... | 424/70.1 |
| 6,579,535 B1 | 6/2003 | Valentine et al. ........... | 424/466 |
| 6,579,543 B1 | 6/2003 | McClung .................... | 424/728 |
| 2001/0032645 A1 | 10/2001 | Cronk et al. .......... | 128/200.24 |
| 2002/0012640 A1 | 1/2002 | Mohammadi et al. ........ | 424/59 |
| 2002/0142015 A1 | 10/2002 | Kumamoto et al. ........ | 424/401 |
| 2002/0173436 A1 | 11/2002 | Sonnenberg et al. ........ | 510/141 |
| 2003/0072842 A1 | 4/2003 | Johnson et al. ................ | 426/3 |
| 2003/0082124 A1 | 5/2003 | Hammer ...................... | 424/64 |
| 2003/0082129 A1 | 5/2003 | Buckingham et al. ... | 424/70.12 |
| 2003/0082271 A1 | 5/2003 | Wolf et al. ..................... | 426/3 |
| 2003/0095936 A1 | 5/2003 | Light ........................... | 424/64 |
| 2003/0113357 A1 | 6/2003 | Bell et al. ................... | 318/439 |
| 2003/0152682 A1 | 8/2003 | Ley et al. ................... | 426/534 |

FOREIGN PATENT DOCUMENTS

| | | |
|---|---|---|
| EP | 1 121 927 A2 | 8/2001 |
| EP | 1 122 233 A1 | 8/2001 |
| JP | 56137891 | * 10/1981 |
| WO | WO 93/23005 | 11/1993 |
| WO | WO 98/07404 | 2/1998 |
| WO | WO 99/07235 | 2/1999 |
| WO | WO 00/45815 | 8/2000 |
| WO | WO 02/051392 | 4/2002 |
| WO | WO2004/011415 | 2/2004 |

OTHER PUBLICATIONS

ACS Symposium Series 867, Challenges in Taste Chemistry and Biology, Sponsored by the ACS Division of Agricultural and Food Chemistry, Chapter 9, Pungent and Tingling Compounds in Asian Cuisine, Galopin, et al, pp. 139–152, 2004.

(Continued)

Primary Examiner—Cecilia J. Tsang
Assistant Examiner—Taylor V. Oh
(74) Attorney, Agent, or Firm—Joseph F. Leightner

(57) ABSTRACT

Described is a genus of menthyl half acid ester derivatives having the structure:

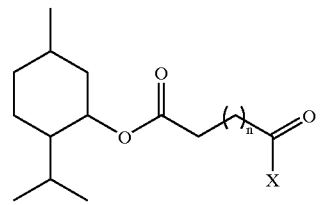

and processes for producing same, wherein n is an integer of from 1 to 5; wherein X is either —OR" or —NRR'; wherein R" is hydrogen, $C_1$–$C_5$ lower alkyl or $C_3$–$C_6$ lower alkenyl; wherein R is hydrogen, $C_1$–$C_5$ lower alkyl, 2-hydroxyethyl or cyclopropyl and wherein R' is hydrogen, methyl or ethyl; with the proviso that when X is —OR", n is an integer of from 3 to 5, having utility for augmenting, enhancing or imparting a taste or cooling effect or refreshing effect in or to an ingestible or topical composition.

38 Claims, No Drawings

OTHER PUBLICATIONS

U.S. Appl. No. 10/411,672, filed Apr. 11, 2003, Dewis et al. Search for Unsaturated Dienoic Acid Compounds, p 1–5, Jul. 15, 2003.

GRAS Flavoring Substances 20, Food Technology, vol. 55, No. 12, Dec. 2001 at p. 53.

Rule, et al, Optical Activity and the Polarity of Substituent Groups Part VIII. Growing–chain Effects and the Ortho–Effect in Benzoic Esters, J.Chem.Soc. 1928 (Part I), pp. 1347–1361.

SciFinder (Nov. 20, 2002; Trademark of Chemical Abstracts Service), to wit: malonamic acid, p–menth–3–yl ester, ±–(8C1) having CAS Registry No. 6129–88–0.

Jaloner, et al, A Molecular Approach to Flavor Synthesis. I. Menthol Esters of Varying Size and Polarity, Journal of Polymer Science:Polymer Chemistry Edition, vol. 18, 2933–2940 (1980).

Ottinger, et al, Systematic Studies on Structure and Physiological Activity of Cyclic Alpha–Keto Enamines, a Novel Class of "Cooling" Compounds, J.Agric.Food Chem., 2001, 49, 5383–5390.

U.S. Appl. No. 10/643,542, filed Aug. 19, 2003, Flammer, et al.

Prior Art Submission Under 37 CFR 1.291.

* cited by examiner

MENTHYL HALF ACID ESTER DERIVATIVES, PROCESSES FOR PREPARING SAME, AND USES THEREOF FOR THEIR COOLING/REFRESHING EFFECT IN CONSUMABLE MATERIALS

FIELD OF THE INVENTION

Derivatives of mono menthyl esters of alkyl dioic acids including mono menthyl half acid esters and the amides thereof which provide refreshing and cooling attributes in the oral cavity, the nasal cavity and on the skin in the substantial absence of any negative taste, aroma and cooling attributes.

BACKGROUND OF THE INVENTION

A significant number of compounds are known to be useful in providing a cooling sensation in the mouth, in the nasal cavity and/or on skin. The best known and most widely used of these is menthol which in addition to olfaction caused a cooling response on cold receptors in the oral cavity, the nasal cavity and on skin.

Since menthol has a strong minty odor, a bitter taste and provides a burning sensation when used in high concentrations, a variety of other menthyl ester-based and menthyl carboxamide-based cooling compounds have been developed, are taught in the prior art and are used in flavor or fragrance applications. Such menthyl ester-based and menthyl carboxamide-based cooling compounds include the menthyl carboxamide, N-ethyl-p-menthane carboxamide, WS-3, trademark of the Warner Lambert Company, disclosed in U.S. Pat. No. 4,150,052, and monomenthyl succinate, monomenthyl-αα-dimethyl succinate, monomenthyl methyl succinate, monomenthyl glutarate, menthyl 2-pyrrolidone-5-carboxylate and monomenthyl 3-methyl maleate, the uses of which are disclosed in U.S. Pat. Nos. 3,111,127; 5,725,865; 5,843,466; 6,365,215 and 6,451,844.

More specifically, U.S. Pat. No. 3,111,127 discloses such monomenthyl esters as monomenthyl succinate, monomenthyl αα-dimethyl succinate and monomenthyl 2-methylmaleate covered by the generic structure:

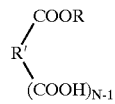

wherein R represents a menthyl radical and R' is selected from the group consisting of 'saturated and unsaturated aliphatic, aromatic and heteroaromatic polycarboxylic acid radicals and substituted analogues thereof and N is the total number of carboxyl groups in the acid from which the ester is derived' for improving the flavoring characteristics when incorporated in a tobacco product. U.S. Pat. No. 4,150,052 discloses the use of N-ethyl p-menthane-3-carboxamide for its physiological cooling action on the skin, and discloses its use in, for example, chewing gum. U.S. Pat. Nos. 5,725,865 and 5,843,466 disclose the use of mono menthyl succinate for its physiological cooling action and disclose its use in, for example, carbonated beverages, alcoholic beverages and chewing gum. U.S. Pat. No. 6,365,215 discloses at Col. 11, line 3, the use of mono menthyl glutarate in oral sensory perception-affecting compositions for use with such consumable materials as chewing gums. U.S. Pat. No. 6,451,844 discloses the use of menthyl 2-pyrrolidone-5-carboxylate (QUESTICE L, Quest International, B.V. of Naarden, Netherlands) having the structure:

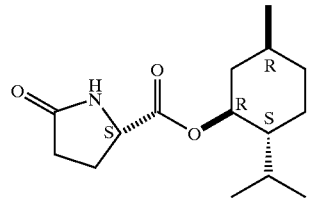

in skin care and hair care compositions for their insect repellency properties.

Furthermore, L-mono menthyl glutarate has been registered as a GRAS flavoring substance, FEMA No. 4006 and, in Smith et al. "GRAS Flavoring Substances 20", *Food Technology*, Vol. 55, No. 12, December 2001 at page 53 is indicated to have uses in nonalcoholic beverages, alcoholic beverages: chewing gum, confectionery frosting, hard candy, soft candy and snack foods.

A number of the mono menthyl half acid ester derivatives found to be useful in the practice of our invention are novel; however those that are disclosed in the prior art together with their respective syntheses, without the disclosure of utilities thereof are the compounds having the structure:

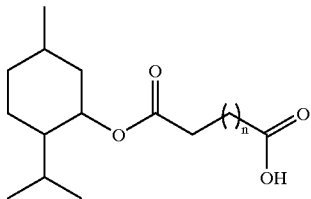

where n is an integer of from 3 up to 5, as follows:

(i) L-menthyl hydrogen adipate (n=3);
(ii) L-menthyl hydrogen piel ate (n=4); and
(iii) L-menthyl hydrogen suberate (n=5)

by Rule et al., "Optical Activity and the Polarity of Substituent Groups Part VIII. Growing chain Effects and the orthoEffect in Benzoic Esters", *J. Chem. Soc.* 1928 (Part I), pp. 1347–136.

In addition, a lower adjacent methylene homologue of the genus of novel compounds of our invention which genus has the structure:

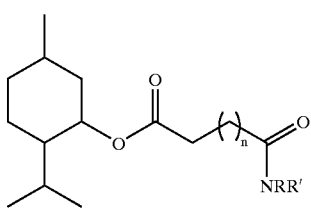

wherein n is an integer of from 1 to 5; wherein R is hydrogen, $C_1$–$C_5$ lower alkyl, 2-hydroxyethyl or cyclopropyl and wherein R' is hydrogen, methyl or ethyl is disclosed in "SciFinder" (Nov. 20, 2002; Trademark of Chemical Abstracts Services), to wit: malonamic acid, pmentb-3-yl ester, (±)-(8CI) having CAS Registry Number 6129-88-0 where the structure is shown below:

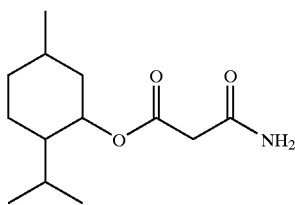

No indication of the use of the compound, malonamic acid, pmenth-3-yl ester, (±)- is set forth in the SciFinder disclosure.

Despite the existence in the prior art and in commerce of such a vast number and variety of cooling agents including mono menthyl ester-based compounds in food, cosmetic and fragrance applications, there still remains a need for cooler compounds which provide strong and substantive refreshing and cooling attributes in the absence of negative taste, negative aroma and negative cooling attributes, and more particularly there still exists a need for cooler compounds which provide good onset of effect, prolonged cooling and economy of use.

SUMMARY OF THE INVENTION

Our invention relates to a process for augmenting, enhancing or imparting a taste or cooling effect or refreshing effect in or to a consumable material which is, in the alternative, a foodstuff, a beverage, a chewing gum, an oral care product, a nasal care product, a cologne, a skin care product, a hair care product, a topical cosmetic product or a medicinal product comprising the step of adding to said consumable material a taste- or cooling effect- or refreshing effect-augmenting, enhancing or imparting quantity and concentration of at least one menthyl half acid ester derivative having the structure:

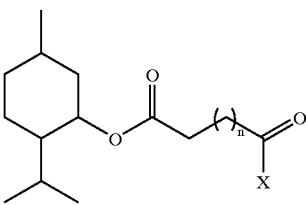

wherein n is an integer of from 1 to 5; wherein X is selected from the group consisting of —OR" and —NRR'; wherein R" is hydrogen, $C_1$–$C_5$ lower alkyl or $C_3$–$C_6$ lower alkenyl; wherein R is hydrogen, $C_1$–$C_5$ lower alkyl, 2-hydroxyethyl or cyclopropyl and wherein R' is hydrogen, methyl or ethyl; with the proviso that when X is —OR", n is an integer of from 3 to 5.

More specifically, our invention is directed to a process for augmenting, enhancing or imparting a taste or cooling or refreshing effect in or to a cosmetic, skin care product, lip gloss, hair care product, cologne, shaving balm, after-shave lotion, dairy product, fruit ice preparation, confectionery, mouth and throat lozenges, cough mixtures, decongestants, antacids, oral analgesics or other medicinal products, chewing gum candy (including hard candy and soft candy), fondants, toothpaste, mouthwashes, mineral water, alcoholic beverage, non-alcoholic beverage, powdered beverage, or other foodstuff comprising the step of adding to a cosmetic, skin care product, lip gloss, hair care product, cologne, shaving balm, after-shave lotion, dairy product, fruit ice preparation, confectionery, lozenges, cough mixtures, decongestants, antacids, oral analgesics or other medicinal product, chewing gum, candy, fondants, toothpaste, mouthwashes, mineral water, alcoholic beverage, non-alcoholic beverage, powdered beverage, or other foodstuff, a taste or cooling or refreshing effect augmenting, enhancing or imparting quantity and concentration of at least one menthyl half acid ester derivative having the structure:

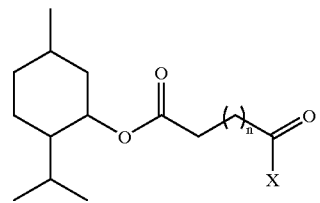

wherein n is an integer of from 1 to 5; wherein X is selected from the group consisting of —OR" and —NRR'; wherein R" is hydrogen, $C_1$–$C_5$ lower alkyl or $C_3$–$C_6$ lower alkenyl; wherein R is hydrogen, $C_1$–$C_5$ lower alkyl, 2-hydroxyethyl or cyclopropyl and wherein R' is hydrogen, methyl or ethyl; with the proviso that when X is —OR", n is an integer of from 3 to 5.

Preferably, each of the menthyl half acid ester derivatives useful in the practice of our invention is a member of genus, the structure which is, in the alternative, one of:

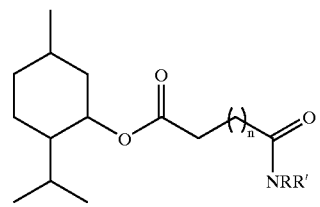

wherein n is an integer of from 3 to 5; wherein

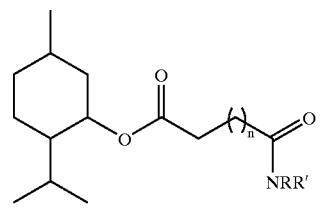

wherein n is an integer from 1 to 5; wherein R is hydrogen, $C_1$–$C_5$ lower alkyl, 2-hydroxyethyl or cyclopropyl and wherein R' is hydrogen, methyl or ethyl.

More preferably, each of the menthyl half acid ester derivatives useful in the practice of our invention is a member of a genus, the structure which is, in the alternative, one of:

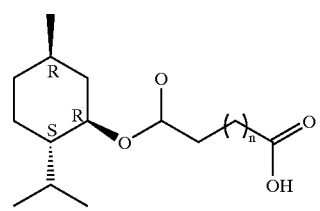

wherein n is an integer of from 3 to 5; or

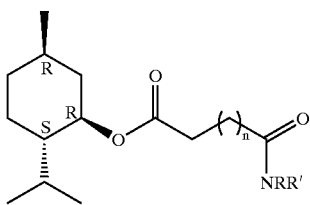

wherein n is an integer of from 1 to 5; wherein R is hydrogen, $C_1$–$C_5$ lower alkyl, 2-hydroxyethyl or cyclopropyl and wherein R' is hydrogen, methyl or ethyl.

Still more preferably, each of the menthyl half acid ester derivatives useful in the practice of our invention is a member of the genus having the structure:

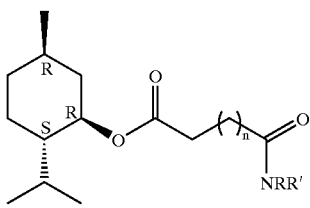

wherein R is, in the alternative, hydrogen, methyl or ethyl; R' is, in the alternative, hydrogen or methyl and n is 1 or 2.

A preferable compound useful in the practice of our invention is mono menthyl adipate having the structure:

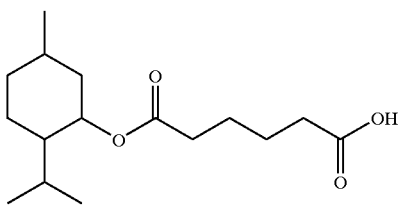

Our invention is also directed to the novel compounds each of which is a member of:

(a) the genus defined by the structure:

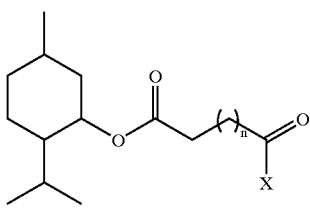

wherein n is an integer of from 1 to 5; wherein X is in the alternative one of —OR" or —NRR'; wherein R" is $C_1$–$C_5$ lower alkyl or $C_3$–$C_6$ lowter alkenyl; wherein R is hydrogen, $C_1$–$C_5$ lower alkyl 2-hydroxyethyl or cyclopropyl and wherein R' is hydrogen, methyl or ethyl; with the proviso that when X is —OR", n is an integer of from 3 to 5; preferably, the sub-genus defined according to the structure:

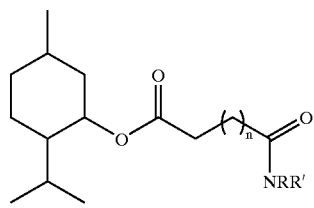

wherein n is an integer of from 1 to 5; wherein R is hydrogen, $C_1$–$C_5$ lower alkyl, 2-hydroxyethyl or cyclopropyl and wherein R' is hydrogen, methyl or ethyl; more preferably, the sub-genus defined according to the structure:

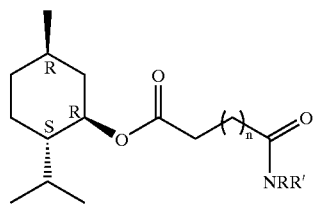

wherein n is an integer of from 1 to 5; wherein R is hydrogen, $C_1$–$C_5$ lower alkyl, 2-hydroxyethyl or cyclopropyl and wherein R" is hydrogen, methyl or ethyl; and most preferably the sub-genus defined according to the structure:

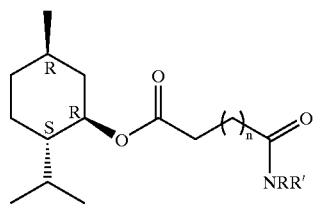

wherein R is, in the alternative, hydrogen, methyl or ethyl; R' is, in the alternative, hydrogen or methyl and n is 1 or 2; and (b) the genus of isomers defined according 10 the structure:

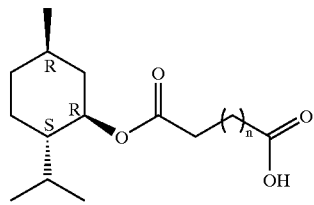

wherein n is an integer of from 3 to 5.

A preferred novel compound useful in the practice of our invention is the novel isomer of L-mono menthyl adipate, having the structure:

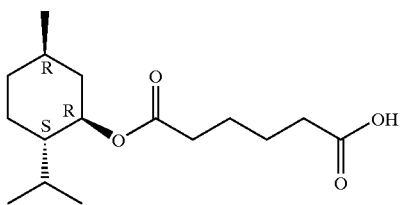

Preferably, the menthyl adipate and/or the aforementioned menthyl adipate isomer, when used in the practice of our invention is(are) utilized in the substantial absence of dimenthyl adipate less than about 2%, having the structure:

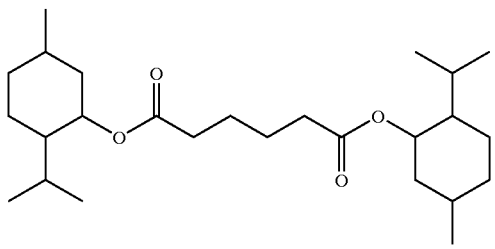

and/or the corresponding isomer thereof, having the structure:

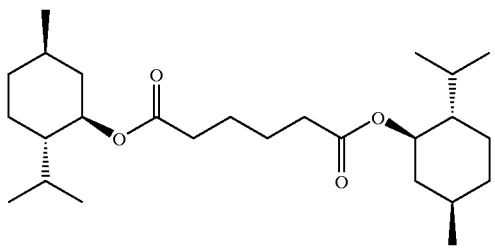

as the case may be, which are preferably substantially all removed from the reaction product prior to utilizing the menthyl adipate and/or corresponding isomer thereof in the practice of our invention.

Our invention is also directed to the synthesis process for producing each of the aforementioned monomenthyl half acid ester derivatives as follows:

(a) A process for producing a menthyl half acid ester derivative having the structure:

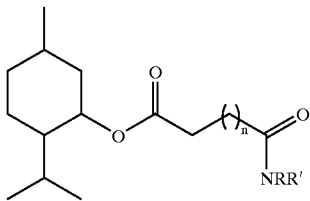

comprising the steps of admixing a compound having the structure:

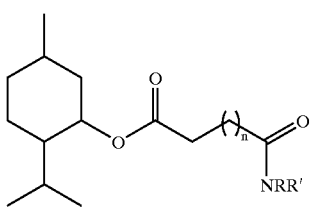

with an inert solvent to form a solution; then admixing the resulting solution with an aliphatic or aromatic tertiary amine base at a temperature in the range of from about 0° C. to about 30° C.; then admixing the resulting product with an oxalyl dihalide while maintaining the reaction temperature in the range of from about 5° C. to about 30° C. thereby forming an intermediate; then admixing the resulting intermediate with an amine having the formula RR'NH at a temperature in the range of from about 0° C. to about 30° C.; and then isolating the compound having the structure:

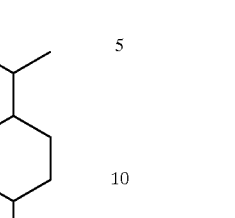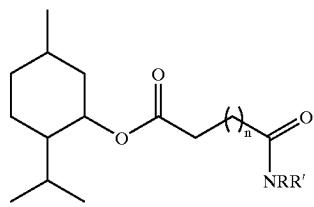

from the resulting reaction product wherein n is an integer of from 1 to 5; wherein R is hydrogen, ($C_1$–$C_5$) lower alkyl, 2-hydroxyethyl or cyclopropyl and wherein R' is hydrogen, methyl or ethyl; and (b) A process for producing a menthyl half acid ester derivative having the structure:

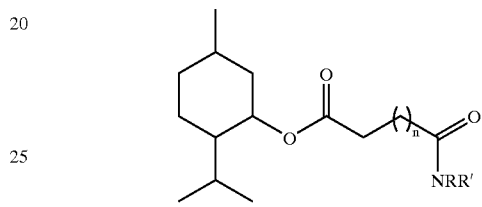

comprising the steps of admixing a compound having the structure:

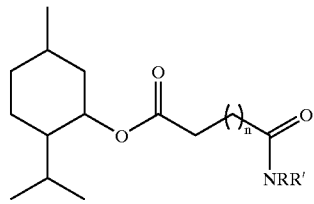

with an inert solvent to form a solution; admixing the resulting solution with a lower alkyl haloformate at a temperature in the range of from about 0° C. up to about 30° C. whereby an intermediate is formed; then cooling the resulting intermediate-containing product to a temperature in the range of from about −30° C. to about +5° C.; then admixing the resulting intermediate-containing product with an aliphatic or aromatic tertiary amine while maintaining the temperature of the mixture at from about −15° C. to about +5° C.; filtering the resulting mixture; cooling the filtrate to a temperature in the range of from about −15° C. to about +5° C.; admixing the resulting product with an amine having the formula RR'NH at a temperature in the range of from about 0° C. to about 30° C.; and then isolating the compound having the structure:

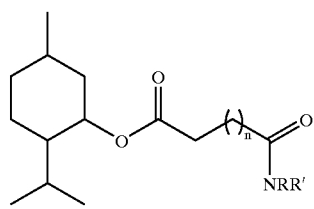

from the resulting reaction product, wherein n is an integer of from 1 to 5; wherein R is hydrogen, $C_1$–$C_5$ lower alkyl, 2-hydroxyethyl or cyclopropyl and wherein R' is hydrogen, methyl or ethyl.

When the novel esters of our invention having the structure:

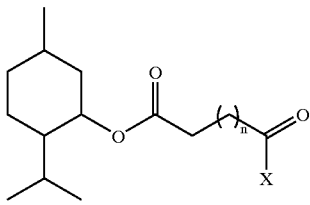

wherein X is —OR" and R" is $C_1$–$C_5$ lower alkyl, such as but not limited to methyl, ethyl, isopropyl, n-propyl, n-butyl, isobutyl, t-butyl, n-pentyl, 2-pentyl, 3-pentyl or 2-methyl-3-butyl, or $C_3$–$C_6$ alkenyl, such as but not limited to 1-propen-1-yl, 2-propen-1-yl, 3-propen-1-yl, 1-buten-2-yl, 2-buten-3-yl, 3-penten-4-yl or 4-hexen-1-yl are desired to be synthesized, the corresponding menthyl half acid ester having the formula:

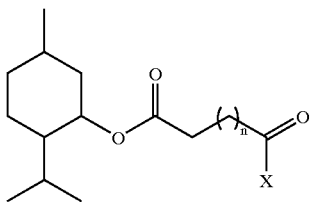

is either:
i. first reacted with a reagent to form the corresponding menthyl half acyl halide ester, using a reagent such as $PCl_3$, $PCl_5$, $SOCl_2$ or an oxalyl dihalide such as oxalyl dichloride and then the resulting menthyl half acyl halide ester is reacted with either the corresponding alcohol, R"OH or its alkali metal alkoxide having the formula R"OM where M is an alkali metal, such as but not limited to sodium, potassium or lithium;
ii. first reacted with AgOH to form the corresponding silver salt and then the resulting silver salt is reacted with the desired halide having the formula R"Z where Z is chloro, bromo or iodo;
iii. reacted with a diazoalkane or diazoalkene of the formula R'''(N═N) wherein R''' is alkylene or alkenylene corresponding to R"; or
iv. mixed with an inert solvent to form a solution; then admixing the resulting solution with an aliphatic or aromatic tertiary amine base at a temperature in the range of from about 0° C. to about 30° C.; then admixing the resulting product with an all haloformate while maintaining the reaction temperature in the range of from about 5° C. to about 30° C. thereby forming an intermediate; then admixing the resulting intermediate with the alcohol, R"OH thereby forming an intermediate; then admixing the resulting intermediate with the alcohol, R"OH thereby forming the ester reaction product.

DETAILED DESCRIPTION OF THE INVENTION

Our invention specifically relates to a process for augmenting, enhancing or imparting a taste or cooling effect or refreshing effect in or to a consumable material which is, in the alternative, a foodstuff, a beverage, a chewing gum, an oral care product, a nasal care product a cologne, a skin care product, a hair care product, a topical cosmetic product or a medicinal product comprising the step of adding to said consumable material a taste- or cooling effect- or refreshing effect-augmenting, enhancing or imparting quantity and concentration of at least one menthyl half acid ester derivative having the structure:

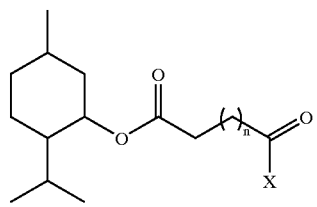

wherein n is an integer of from 1 to 5; wherein X is in the alternative one of —OR" or —NRR'; wherein R" is in the alternative, one of hydrogen, $C_1$–$C_5$ lower alkyl or $C_3$–$C_6$ lower alkenyl; wherein R is hydrogen, $C_1$–$C_5$ lower alkyl, 2-hydroxyethyl or cyclopropyl and wherein R' is hydrogen, methyl or ethyl; with the proviso that when X is —OR", n is an integer of from 3 to 5 as well as to processes for preparing sub-genera of same and to novel sub-genera of the aforementioned genus as defined supra and exemplified infra.

The flavor and sensory characteristics of members of the aforementioned genus are set forth in the following Table 1:

TABLE I

| X | | | | Compound | Cooling | Onset | |
|---|---|---|---|---|---|---|---|
| —COR" | —NRR' | | | (at use level of | Duration | Time | |
| R" | R | R' | n | 25 ppm in water) | (Minutes) | (Seconds) | Taste/Sensory Profile |
| N/A | H | H | 1 | Butanoic acid, 4-amino-4-oxo, (5-methyl-2-(1-methylethyl)cyclohexyl) ester, (1R-(1α,2β,5α))- | 7.5 | 8–25 | Pleasant cooling effect on lips and gums; fruity aroma nuance |
| N/A | Me | H | 1 | Butanoic acid, 4-methylamino-4-oxo, (5-methyl-2-(1-methylethyl)cyclohexyl) ester, (1R-(1α,2β,5α))- | 7 | 15–25 | Natural cooling on tongue, gums palate and inner part of lips |
| N/A | Me | Me | 1 | Butanoic acid, 4-dimethylamino-4-oxo, (5-methyl-2-(1-methylethyl)cyclohexyl) ester, | 11.25 | 25 | Cooling and refreshing on tongue, palate and front gums; fruity flavor with |

TABLE I-continued

| X | | | | Compound | Cooling | Onset | |
|---|---|---|---|---|---|---|---|
| —COR" | | —NRR' | | (at use level of | Duration | Time | |
| R" | R | R' | n | 25 ppm in water) | (Minutes) | (Seconds) | Taste/Sensory Profile |
| | | | | (1R-(1α,2β,5α))- | | | estery topnotes and sour undertones |
| N/A | Et | H | 1 | Butanoic acid, 4-ethylamino-4-oxo, (5-methyl-2-(1-methylethyl)cyclohexyl) ester, (1R-(1α,2β,5α))- | 7 | 35 | Substantive pleasant cooling and tingling on top palate |
| N/A | Me | H | 2 | Pentanoic acid, 4-methylamino-4-oxo, (5-methyl-2-(1-methylethyl)cyclohexyl) ester, (1R-(1α,2β,5α))- | 5 | 20 | Clean, pleasantly icy on tongue and hard palate |
| N/A | CH₂CH₂—OH | H | 1 | Butanoic acid, 4-(2-hydroxyethyl)amino-4-oxo, (5-methyl-2-(1-methylethyl)cyclohexyl) ester, (1R-(1α,2β,5α))- | 15 | 11 | Fruity, minty flavor nuances; substantive cooling of palate and warming sensation in throat; overall simultaneous warming and cooling |
| —OH | N/A | N/A | 3 | Hexanedioic acid, mono(5-methyl-2-(1-methylethyl)cyclohexyl)ester, (1R-(1α,2β,5α))- | 10.5 | 34 | Increasing pleasant icy-type cooling over time for tongue, lower gums; pleasant sour menthol and medicinal flavor nuances |

The properties of the menthyl half acid ester derivatives as set forth in the aforementioned Table I is indicative that the menthyl half acid ester derivatives of our invention are useful for augmenting, enhancing or imparting a taste or cooling or refreshing effect in or to a cosmetic, skin care product, lip gloss, hair care product, cologne: shaving balm, after-shave lotion, dairy product, fruit ice preparation, confectionery, mouth and throat lozenges, cough mixtures, decongestants, antacids, oral analgesics or other medicinal products, chewing gum, candy (including hard candy and soft candy), fondants, toothpaste, mouthwashes, mineral water, alcoholic beverage, non-alcoholic beverage, powdered beverage, or other foodstuff as a result of adding to a cosmetic, skin care product, lip gloss, hair care product, cologne, shaving balm, after-shave lotion, dairy product, fruit ice preparation, confectionery, lozenges, cough mixtures, decongestants, antacids, oral analgesics or other medicinal product, chewing gum, candy, fondants, toothpaste, mouthwashes, mineral water, alcoholic beverage, non-alcoholic beverage, powdered beverage, or other foodstuff, a taste or cooling or refreshing effect augmenting, enhancing or imparting quantity and concentration of at least one menthyl half acid ester derivative having the structure:

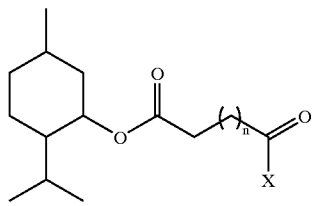

wherein n is an integer of from 1 to 5; wherein X is selected from the group consisting of —OR" and —NRR'; wherein R" is hydrogen, $C_1$–$C_5$ lower alkyl or $C_3$–$C_6$ lower alkenyl; wherein R is hydrogen, $C_1$–$C_5$ lower alkyl, 2-hydroxyethyl or cyclopropyl and wherein R' is hydrogen, methyl or ethyl; with the proviso that when X is 13 OR", n is an integer of from 3 to 5.

Accordingly, the following Table II sets forth examples of processes and compositions where the menthyl half acid ester derivatives of our invention are utilized, as set forth in the immediately preceding paragraph. Each of the useful ingredients set forth in the cited references, including the examples thereof is usable in the practice of our invention:

TABLE II

| Nature of Use of the menthyl half acid ester derivatives of our invention | Reference containing examples where the menthyl half acid ester derivatives of our invention are utilizable |
|---|---|
| Chewing gum and confectionery composition | U.S. Pat. No. 5,009,893 |
| Flavored calcium supplements, beverages, chewing gum and oral care products | U.S. Pat. No. 6,251,463 |
| Cough Treatment Compositions | U.S. Pat. No. 6,391,886 |
| Sugar and sugarless chewing gums | U.S. Pat. No. 6,455,080 |
| Non-alcoholic fruit beverages | U.S. Pat. No. 6,572,914 |
| Composition for topical application to skin | U.S. Pat. Nos. 6,579,543 and 6,451,844 |
| Chewable sweetened medicinal tablets | U.S. Pat. No. 6,579,535 |
| Moisturizing composition for skin | U.S. Pat. No. 6,579,516 |
| Anti-infective periodontic composition | U.S. Pat. No. 6,579,514 |
| Hygiene mouth spray formulation | U.S. Pat. No. 6,579,513 |
| Multiphase soap | Published U.S. patent application 2002/0173436 A1 published Nov. 21, 2002 |
| Topical cosmetic skin care composition in form of lotion, cream or gel | Published U.S. patent application 2003/0113357 A1 published Jun. 19, 2003 |
| Nasal strips and dilators | Published U.S. patent application 2001/0032645 A1 published Oct. 25, 2001 |
| Chewing gum | Published U.S. patent application 2003/0072842 A1 published on Apr. 17, 2003 |
| Cosmetic compositions for stressed skin under extreme conditions | Published U.S. application 2002/0012640 A1 published on Jan. 31, 2002 |

TABLE II-continued

| Nature of Use of the menthyl half acid ester derivatives of our invention | Reference containing examples where the menthyl half acid ester derivatives of our invention are utilizable |
|---|---|
| Chewing Gum | Published U.S. application 2003/0082271 A1 published on May 1, 2003 |
| Oral care compositions | PCT Published Application WO 93/23005 |
| Aqueous skin cosmetic compositions | PCT Published Application WO 98/07404 |
| Confectionery compositions and chewing gum | PCT Published Application WO 99/07235 |
| Compositions for alleviating 'hot flashes' | PCT Published Application WO 00/45815 |
| Liquid lipstick | Published U.S. application 2003/0082124 A1 published on May 1, 2003 |
| Lip gloss composition | Published U.S. application 2003/0095936 A1 published on May 22, 2003 |
| Hair care and skin care compositions | Published U.S. application 2003/0082129 A1 published on May 1, 2003 |
| Breath-Freshening chewing gums | PCT Published Application WO 02/051392 A1 |

Examples of the novel compounds of our invention, covered by the genus having the structure:

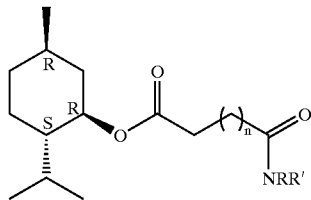

are as follows:

Butanoic acid, 4-amino-4-oxo, (5-methyl-2-(1-methylethyl) cyclohexyl)ester, (1α, 2β,5α)-(±)-
Butanoic acid, 4-methylamino-4-oxo, (5-methyl-2-(1-methylethyl)cyclohexyl)ester, -(1α,2β,5α)-(±)-
Butanoic acid, 4-dimethylamino-4-oxo, (5-methyl-2-(1-methylethyl)cyclohexyl)ester, -(1α,2β,5α)-(±)-
Butanoic acid, 4-ethylamino-4-oxo, (5-methyl-2-(1-methylethyl)cyclohexyl)ester, -(1α,2β,5α)-(±)-
Pentanoic acid, 4-methylamino-4-oxo, (5-methyl-2-(1-methylethyl)cyclohexyl)ester, -(1α,2β,5α)-(±)-
Hexanoic acid, 4-methylamino-4-oxo, (5-methyl-2-(1-methylethyl)cyclohexyl)ester, -(1α,2β,5α))-(±)-
Butanoic acid, 4-(2-hydroxyethyl)amino-4-oxo, (5-methyl-2-(1-methylethyl)cyclohexyl)ester, (1α,2β,5α))-(±)-
Butanoic acid, 4-amino-4-oxo, (5-methyl-2-(1-methylethyl) cyclohexyl)ester, -(1R-(1α,2β,5α))-
Butanoic acid, 4-methylamino-4-oxo, (5-methyl-2-(1-methylethyl)cyclohexyl)ester, -(1R-(1α,2β,5α))-
Butanoic acid, 4-dimethylamino-4-oxo, (5-methyl-2-(1-methylethyl)cyclohexyl)ester, -(1R-(1α,2β,5α))-
Butanoic acid, 4-methylamino-4-oxo, (5-methyl-2-(1-methylethyl)cyclohexyl)ester, -(1R-(1α,2β,5α))-
Pentanoic acid, 4-methylamino-4-oxo, (5-methyl-2-(1-methylethyl)cyclohexyl)ester, -(1R-(1α,2β,5α))-
Hexanoic acid, 4-methylamino-4-oxo, (5-methyl-2-(1-methylethyl)cyclohexyl)ester, -(1R-(1α,2β,5α))-; and
Butanoic acid, 4-(2-hydroxyethyl)amino-4-oxo, (5-methyl-2-(1-methylethyl)cyclohexyl)ester, (1R-(1α,2β,5α))-

As used herein the term, olfactory effective amount is understood to mean the amount of compound in flavor compositions, oral care compositions and articles, nasal care compositions and articles, skin care compositions, hair care compositions, cosmetic compositions, and other consumable materials as defined herein, the individual component will contribute to its particular olfactory characteristics, but the flavor, taste and aroma effect on the overall composition will be the sum of the effects of each of the cooling and/or refreshing and/or pungent flavor and/or sense imparting, augmenting or enhancing ingredients. As used herein taste effects include cooling, refreshing and pungent effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of menthyl half acid ester derivatives, including menthyl half acid esters or N-alkyl alkamic acid menthyl esters used in products is greater than 1 parts per million, generally provided at a level of from about 5 parts per million to about 50,000 parts per million in the finished product, more preferably from about 10 parts per million to about 1000 parts per million by weight.

The usage levels of menthyl half-acid ester derivatives, including menthyl half acid esters or N-alkyl alkamic acid menthyl esters vary depending on the product in which the menthyl half-acid ester derivatives including menthyl half acid esters or N-alkyl alkamic acid menthyl esters are employed.

Thus, with reference to the use of the menthyl half acid ester derivatives of our invention in alcoholic beverages, the usage level is from about 5 parts to about 200 parts per million, preferably from about 20 to about 150 and most preferably from about 30 to about 80 parts per million by weight.

With reference to the use of the menthyl half acid ester derivatives of our invention in non-alcoholic beverages including carbonated beverages and fruit drinks, the non-alcoholic beverages are flavored at levels of from about 1 parts to about 30 parts per million, preferably from about 5 parts to about 15 parts per million.

With reference to the use of the menthyl half acid ester derivatives of our invention in toothpaste, the toothpaste can be satisfactorily flavored by using menthyl half acid ester derivatives including menthyl half acid esters or N-alkyl alkamic acid menthyl esters at levels of from about 200 to about 700 parts per million, more preferably from about 300 to about 600 parts per million by weight and most preferable from about 350 up to about 550 parts per million by weight.

With reference to the use of the menthyl half acid ester derivatives of our invention in candy products including hard candy, the candy can be flavored at levels of from about 500 to about 2500; preferably from about 1000 to about 2000 parts per million by weight.

With reference to the use of the menthyl half acid ester derivatives of our invention in chewing gum, chewing gum usage levels are from about 800 to about 3000 ppm, preferably from about 1500 to about 2500 parts per million by weight.

The term foodstuff as used herein includes both solid and liquid ingestible materials for man or animals, which materials usually do, but need not, have nutritional value. Thus, foodstuffs include meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the menthyl half-acid ester derivatives including menthyl half acid esters or N-alkyl alkamic acid menthyl esters compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the menthyl half acid esters or N-alkyl alkamic acid menthyl esters of our invention; (2) that they be organoleptically compatible with the menthyl half acid ester or N-alkyl alkamic acid menthyl ester derivative(s) of our invention whereby the flavor of the ultimate consumable material to which the menthyl half acid esters or N-alkyl alkamic acid menthyl esters are added is not detrimentally affected by the use of the adjuvant; and (3) that they be ingestible acceptable and thus nontoxic or otherwise nondeleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the menthyl half acid esters or N-alkyl alkamic acid menthyl esters of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillin, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclopentenolone; benzaldehyde; valerian oil; 3,4-dimethoxyphenol; amyl acetate; amyl cinnamate; γ-butyryl lactone; furfural; trimethylpyrazine; phenyl acetic acid: isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methylpyrazine; 2-ethyl-3-methylpyrazine; tetramethylpyrazine; polysulfides; dipropyl disulfide; methyl benzyl disulfide; alkyl thiophene; 2,3-dimethyl thiophene; 5-methyl furfural; acetyl furan; 2,4-decadienal; guaiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysleine; hydrolyzed vegetable protein; 2-methylfuran-3-thiol; 2-methyldihydroforan-3-thiol; 2,5-dimethylfuran-3-thiol; hydrolyzed fish protein; tetramethylpyrazine; propyl propenyl disulfide; propyl propenyl trisulfide; diallyl disulfide; diallyl disulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolne; and 4-methyl-2-(methylthiomethyl)-1,3-dithiolane. These and other flavor ingredients are provided in U.S. Pat. Nos. 6,110,520 and 6,333,180.

The menthyl half acid ester derivatives including the menthyl half acid esters or N-alkyl alkamic acid menthyl esters of our invention or compositions incorporating them, as mentioned above, can be combined with one or more vehicles or carriers for adding them to the particular product. Vehicles can be water-soluble or oil-soluble; and can be edible or otherwise suitable materials such as ethyl alcohol, propylene glycol, water, triacetin, vegetable oil, triethyl citrate and the like, as described supra. Carriers include materials such as gum arabic, carrageenan, xanthan gum, guar gum and the like.

Menthyl half acid ester derivatives including menthyl half acid esters or N-alkyl alkamic acid menthyl esters prepared according to our invention can be incorporated with the carriers by conventional means such as spray-drying, extrusion, drum-drying and the like. Such carriers can also include materials for co-acervating the menthyl half-acid ester derivatives including menthyl half acid esters or N-alkyl alkamic acid menthyl esters of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of menthyl half acid ester derivatives including menthyl half acid esters or N-alkyl alkamic acid menthyl esters utilized should be sufficient to impart the desired flavor characteristic to the product, but on the other hand, the use of an excessive amount of methyl half acid ester derivatives including menthyl half acid esters and/or N-alkyl alkamic acid menthyl esters is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors: the type of storage, if any, to which the product will be subjected; and the pre-consumption treatment such as baking frying and so on, given to the product by the ultimate consumer. Accordingly, the terminology effective amount and sufficient amount is understood in the context of the present invention to be quantitatively adequate to alter the flavor of the foodstuff.

With reference to the novel compounds of our invention, according to the generic structure:

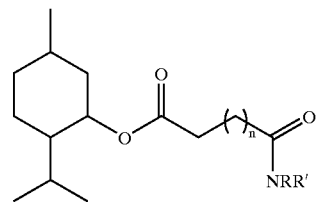

or the generic structure:

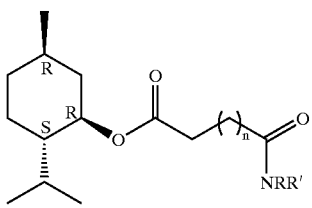

the synthesis of N-alkyl alkamic acid menthyl esters n=1–5 is effected by means of the reaction of menthyl half acid esters with an oxalyl dihalide, preferably oxalyl chloride in the presence of an aliphatic or aromatic tertiary amine base, preferably pyridine or 4(N,N-dimethylamino)pyridine. Subsequent quench of the intermediate with amine, added either directly or in solution, furnishes the N-alkyl alkamic acid menthyl esters according to the exemplary scheme:

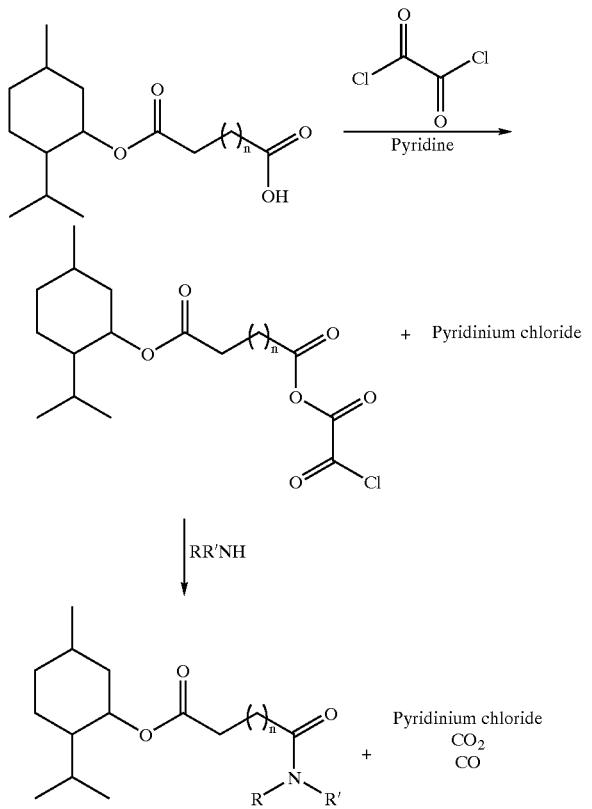

or, in the case of specific isomer production, the exemplary scheme:

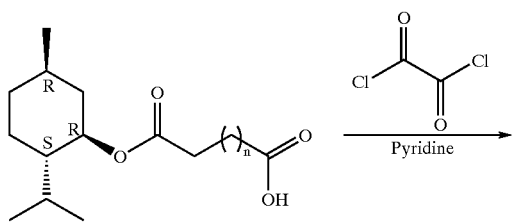

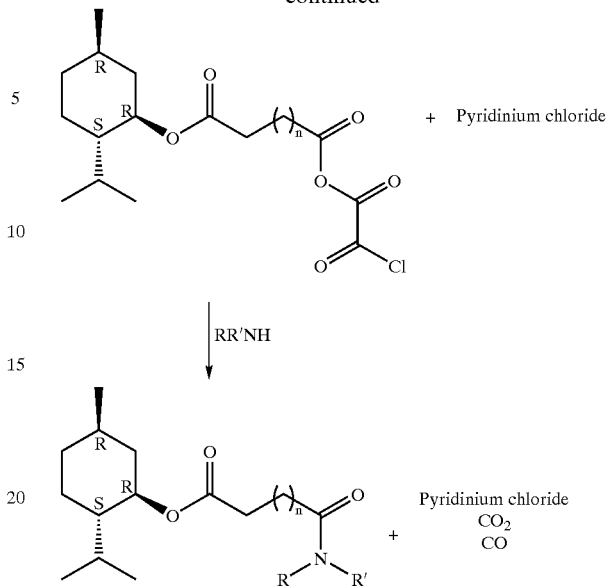

as set forth in examples herein. The acid is dissolved in an inert solvent such as n-hexane, toluene, chloroform, tetrahydrofuran or dichloromethane to which the aliphatic or aromatic amine base such as pyridine is added in 1.2 to 3.2 equivalents at a temperature ranging from 0° C. to room temperature, most preferably from 10° C. to 20° C. While the resulting solution is maintained at a temperature in the range of from about 5° C. to about 30° C. and oxalyl dihalide, e.g. oxalyl dichloride is added in 1.1 to 2.7 equivalents such that the temperature range is below 30° C. and the mixture aged for 30–120 minutes. The amine having the formula RR'NH is added in 1.0 to 7.0 equivalents either neat or as a solution in an inert solvent such as tetrahydrofuran (THF) at a temperature in the range of from about 0° C. to about 30° C. and the reaction mass is aged for about 1–3 hours at room temperature.

The mixture is filtered, the filtrate is concentrated and the crude product is re-dissolved in an inert solvent such as n-hexane, toluene, chloroform, tetrahydrofuran, dichloromethane, or mixtures thereof. The organic solution is then washed with 10% hydrogen chloride, 5% sodium hydroxide and finally aqueous sodium chloride. The solution is then dried using a drying material such as anhydrous magnesium sulfate and solvent removed.

The crude product is purified by recrystallization from an inert solvent such as n-hexane or made as a pot bottom product depending on the physical properties.

The reaction occurs in 41–70% mole yield based on starting half acid.

Alternatively the synthesis of the novel N-alkyl alkamic acid menthyl esters of our invention wherein n=1–5 is effected by means of the reaction of menthyl half acid esters with a lower alkyl haloformate such as ethyl chloroformate in the presence of an aliphatic or aromatic tertiary amine such as triethylamine. Subsequent quench of the intermediate with an amine having the formula RR'NH (added either directly or in solution)furnishes the N-alkyl alkamic acid menthyl esters according to the exemplary reaction scheme:

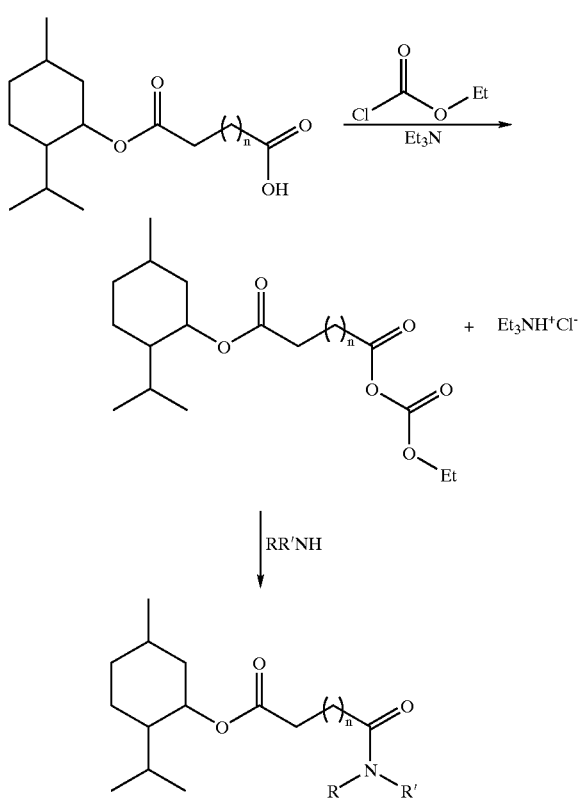

or the exemplary reaction scheme:

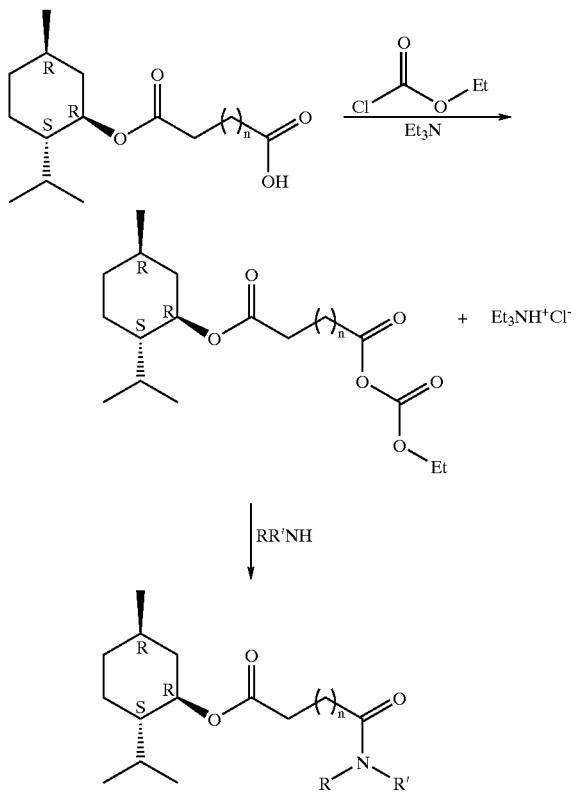

as set forth in examples herein. The acid is dissolved in an inert solvent such as n-hexane, toluene, chloroform, tetrahydrofuran, dichloromethane or mixtures thereof to which the alkyl haloformate, for example, ethyl chloroformate is added in 1.0 to 2.0 equivalents at a temperature ranging from 0° C. to 30° C., most preferably from 10° C. to 20° C. The resulting intermediate-containing solution is cooled to from about 15° C. to about +5° C., and an aliphatic or aromatic tertiary amine such as triethylamine is added in 1.0 to 2.0 equivalents such that the temperature range is from about 0° C. and the intermediate-containing mixture aged for 1–3 hours.

The intermediate-containing mixture is filtered, and the filtrate cooled to a temperature in the range of from about −15° C. to +5° C. The amine having the formula RR'NH is added in 1.0 to 3.0 equivalents either neat, as a solution in a solvent such as THF, or in water in the case of ammonia at a temperature in the range of from about 0° C. to about 30° C., and the reaction mass is aged for about 1–3 hours at room temperature.

The reaction mass is quenched with 10% aqueous acid such as hydrochloric acid, washed with a salt solution such as a sodium chloride solution, dried and the solvent removed.

The crude product is purified by recrystallization from an inert solvent such as n-hexane or made as a pot bottom product depending on the physical properties.

The menthyl half acid ester starting materials for the aforementioned processes having the structures:

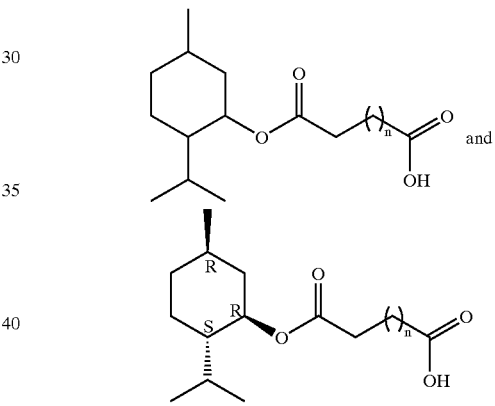

are prepared in accordance with the processes as set forth in Rule et al., "Optical Activity and the Polarity of Substituent Groups Part VIII. Growing-chain Effects and the ortho-Effect in Benzoic Esters", *J. Chem. Soc.* 1928 (Part I), pp. 1347–1361; U.S. Pat. No. 3,111,127; U.S. Pat. No. 5,725,865 and Jabloner et al. "A Molecular Approach to Flavor Synthesis. I. Menthol Esters of Varying Size and Polarity" *J. of Polymer Science*, Vol. 18, pages 2933–40((1980).

The menthyl half acid ester derivatives including menthyl half acid esters or N-alkyl alkamic acid menthyl esters of the present invention can be admixed with other flavoring agents and incorporated into foodstuffs and other product using techniques well known to those with ordinary skill in the art. Most commonly the menthyl half acid ester derivatives including the menthyl half-acid esters or N-alkyl alkamic acid menthyl esters are simply admixed using the desired ingredients within the proportions stated.

The following are provided as specific embodiments of the present invention. Other modifications of this invention will be readily apparent to those skilled in the art, without departing from the scope of this invention. As used herein, both specification and following examples all percentages are weight percent unless noted to the contrary.

EXAMPLE 1

Preparation of Materials of the Present Invention

The following reaction sequences were used to prepare the specific compounds described, by the NMR data set forth below:

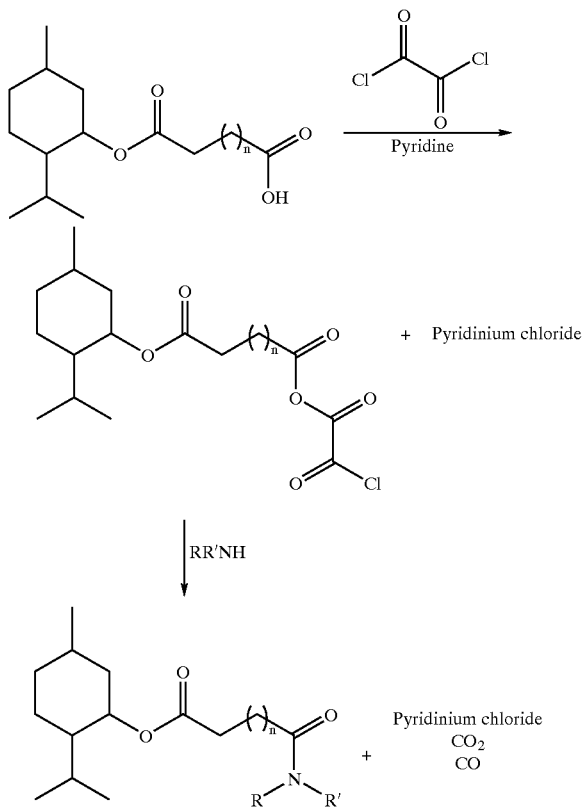

The acid was dissolved in dichloromethane to which pyridine was added in 1.2 to 3.2 equivalents at a temperature ranging from 0° C. to room temperature, most preferably from 10° C. to 20° C. While maintaining the temperature at about 10° C.–20° C., oxalyl chloride was added in 1.1 to 2.7 equivalents and the mixture aged for 30–120 minutes. The amine having the formula RR'NH was added in 1.0 to 7.0 equivalents either neat or as a solution in THF and the reaction was aged for about 1–3 hours at room temperature.

The mixture was filtered, the filtrate was concentrated and the crude product was re-dissolved in dichloromethane. The organic solution was then washed with 10% hydrogen chloride, 5% sodium hydroxide and finally aqueous sodium chloride. The solution was then dried with magnesium sulfate and solvent removed.

The crude product is purified by recrystallization from hexane or made as a pot bottom product depending on the physical properties.

The reaction occurred in 41–70% mole yield based on starting half acid:

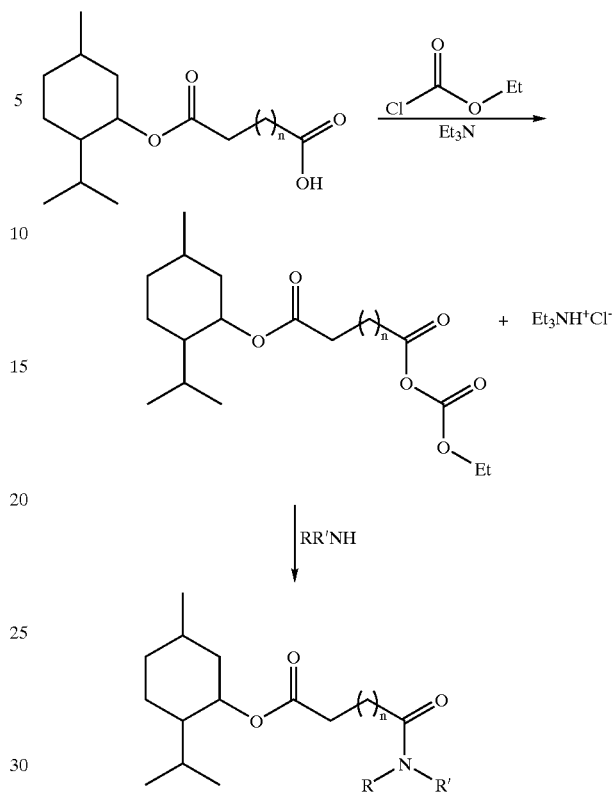

The acid was dissolved in dichloromethane to which ethyl chloroformate was added in 1.0 to 2.0 equivalents at a temperature ranging from 0° C. to room temperature, most preferably from 10° C. to $_{20}$° C. The resulting solution was cooled to –30° C. to +5° C., and triethylamine was added in 1.0 to 2.0 equivalents such that the temperature range was 15° C. to +5° C. and the mixture aged for 1–3 hours.

The mixture was filtered, and the filtrate cooled to –15° C. to +5° C. The amine having the formula RR'NH was added in 1.0 to 3.0 equivalents either neat, as a solution in THF, or in water in the case of ammonia and the reaction as aged for about 1–3 hours at room temperature.

The reaction was quenched with 10% aqueous hydrogen chloride, washed with sodium chloride solution, dried and the solvent removed.

The crude product was purified by recrystallization from hexane or made as a pot bottom product depending on the physical properties.

The reaction occurred in 18–68% mole yields based on starting half acid.

The following examples I(A)–I(J) set forth syntheses of specific menthyl half acid esters and amides of our invention; and include NMR data.

Example I(A)

Butanoic acid, 4-amino-4-oxo, (5-methyl-2-(1-methylethyl)cyclohexyl)ester, (1R-(1α,2β,5α))-

Monomenthyl succinate 1 eq, ethyl chloroformate 1.5 eq, triethylamine 1.5 eq, ammonia (30% in water) 2.0 eq, yield=48% as a white solid.

0.75 ppm (3H, d, J=6.96 Hz), 0.83 ppm (1H, m), 0.89 ppm (6H, 2d, J=7.02 and 6.54 Hz), 0.92–1.11 ppm (2H, m), 1.37 ppm (1H, m), 1.48 ppm (1H, m), 1.67 ppm (2H, m), 1.876 ppm (1H, d, 3=2.70 Hz, of quintet or higher, J=6.98 Hz), 1.97 ppm (1H, m), 2.53 ppm (2H, t, J=6.24 Hz), 2.64 ppm (2H, t, J=6.59 Hz), 4.69 ppm (1H, d, J=4.39 Hz, of t, J=10.89 Hz), 5.89 ppm (2H, br s)

Example I(B)

Butanoic acid, 4-methylamino-4-oxo, (5-methyl-2-(1-methylethyl)cyclohexyl)ester, (1R-(1α,2β,5α))

Monomenthyl succinate 1 eq, oxalyl chloride 2.7 eq, pyridine 3.2 eq, methylamine (2.0M in THF) 4.0 eq, yield=56% as a white solid.

0.75 ppm (3H, d, J=6.96 Hz), 0.84 ppm (1H, m), 0.89 ppm (6H, 2d, J=7.02 and 6.56 Hz), 0.93–1.10 ppm (2H, m), 1.37 ppm (1H, m), 1.47 ppm (1H, m), 1.66 ppm (2H, m), 1.84 ppm (1H, d, J=2.72 Hz, of quintet or higher, J=6.98 Hz), 1.98 ppm (3H, m), 2.48 ppm (2H, t, J=6.92 Hz), 2.65 ppm (2H, t, 3=6.71 Hz), 2.79 ppm (3H, d, J=4.83 Hz), 4.68 ppm (1H, d, J=4.36 Hz, of t, J=10.88 Hz), 6.06 ppm (1H, br s).

Example I(C)

Butanoic acid, 4-dimethylamino-4-oxo, (5-methyl-2-(1-methylethyl)cyclohexyl)ester, (1R-(1α,2β,5α))-

Monomenthyl succinate 1 eq, oxalyl chloride 2.7 eq, pyridine 3.2 eq, dimethylamine (2.0M in THF) 4.0 eq, yield=18% as a yellow liquid.

0.76 ppm (3H, d, J=6.96 Hz), 0.85 ppm (1H, m), 0.89 ppm (6H, 2d, 3=7.03 and 6.56 Hz), 0.92–1.10 ppm (2H, m), 1.33–1.50 ppm (2H, m), 1.67 ppm (2H, m), 1.87 ppm (1H, d, J=2.67 Hz, of quintet or higher, J=6.98 Hz), 2.00 ppm (1H, m), 2.64 ppm (4H, m), 2.99 ppm (6H, m), 4.68 ppm (1H, d, J=4.37 Hz, of t, J=10.88 Hz).

EXAMPLE I(D)

Butanoic acid, 4-ethylamino-4-oxo, (5-methyl-2-(1-methylethyl)cyclohexyl)ester, (1R-(1α,2β,5α))-

Monomenthyl succinate 1 eq, oxalyl chloride 2.7 eq, pyridine 3.2 eq, ethylamine (2.0M in THF) 7.0 eq, yield=46% as a yellow liquid.

0.75 ppm (3H, d, 3=6.97 Hz), 0.85 ppm (1H, m), 0.89 ppm (6H, 2d, J=7.01 and 6.56 Hz), 0.92–1.07 ppm (2H, m), 1.13 ppm (3H, t, 3=7.28 Hz), 1.37 ppm(1H, m), 1.48 ppm (1H, m), 1.65–1.69 ppm (2H, m), 1.84 ppm (1H, d, J=2.61 Hz, of quintet or higher, J=6.93 Hz), 1.98 ppm (3H, m), 2.46 ppm (2H, t, J=6.92 Hz), 2.65 ppm (2H, t, J=6.77 Hz), 3.28 ppm (2H, quintet, J=6.60 Hz), 4.69 ppm (1H, d, J=4.32 Hz, of t, J=10.87 Hz), 5.94 ppm (1H, br s).

Example I(E)

Butanoic acid, 4-(2-hydroxyethyl)amino-4-oxo, (5-methyl-2-(1-methylethyl)cyclohexyl) ester, (1R-(1α,2β,5α))-

Monomenthyl succinate 1 eq, ethyl chloroformate 1.5 eq, triethylamine 1.5 eq, ethanolamine 3.0 eq, yield=68% as a white solid.

0.75 ppm (3H, d, 1=6.96 Hz), 0.85 ppm (1H, m), 0.90 ppm (6H, 2d, J=7.02 and 6.54 Hz), 0.93–1.07 ppm (2H, m), 1.38 ppm (1H, m), 1.46 ppm (1H, m), 1.68 ppm (2H, m), 1.84 ppm (1H, d, J=2.68 Hz, of quintet or higher, J=6.98 Hz), 1.96 ppm (1H, m), 2.49 ppm (2H, t, J=6.80 Hz), 2.67 ppm (2H t, J=6.85 Hz), 2.75–3.03 ppm (1H, br s), 3.42 ppm (2H, m), 3.71 ppm (2H, t, J=5.00 Hz), 4.69 ppm (1H, d, 1=4.40 Hz, of t, J=10.89 Hz), 6.23 ppm (1H, br s)

Example I(F)

Butanoic acid, 4-(2-methylpropyl)amino-4-oxo, (5-methyl-2-(1-methylethyl)cyclohexyl) ester, (1R-(1α,2β, 5α))-

Monomenthyl succinate 1 eq, ethyl chloroformate 1.5 eq, triethylamine 1.5 eq, isobutylamine 3.0 eq, yield=48% as a yellow syrup.

0.74 ppm (3H, d, J=6.96 Hz), 0.85 ppm (1H, m), 0.90 ppm (12H, 2d[6H], J=7.38 and 6.55 Hz, and d[6H], J=6.76 Hz), 0.96–1.09 ppm (2H, m), 1.37 ppm (1H, m), 1.46 ppm (1H, m), 1.67 ppm (2H, m), 1.76 ppm (1H, nonet, J=6.73 Hz), 1.84 ppm (1H, d, J=2.66 Hz, of quintet or higher, J=6.97 Hz), 1.97 ppm (3H, m), 2.47 ppm (2H, t, J=6.86 Hz), 2.65 ppm (2H, t, J=6.76 Hz), 3.07 ppm (2H, t, J=6.43 Hz), 4.69 ppm (1H, d, J=4.40 Hz, of t, J=10.88 Hz), 5.91 ppm (1H, br s).

Example I(G)

Pentanoic acid, 4-methylamino-4-oxo, (5-methyl-2-(1-methylethyl)cyclohexyl) ester, (1R-(1α,2β,5α))-

Monomenthyl glutarate 1 eq. oxalyl chloride 1.6 eq. pyridine 1.7 eq, methylamine (2.0M in THF) 3.0 eq, yield=70% as a white solid.

0.75 ppm (3H, d, J=6.97 Hz), 0.85 ppm (1H, m). 0.90 ppm (6H, 2d, J=6.99 and 6.55 Hz), 0.96 ppm (1H, m), 1.00–1.07 ppm (1H, m), 1.36 ppm (1H, m), 1.48 ppm (5H, m), 1.64–1.70 ppm (2H, m), 1.84 ppm (1H, d, J=2.61 Hz, of quintet or higher, J=6.98 Hz), 1.97 ppm (3H, m), 2.23 ppm (2H, t, J=7.39 Hz), 2.35 ppm (2H, t, J=7.25 Hz), 2.81 ppm (3H, d, J=4.86 Hz), 4.68 ppm (1H, d, 1=4.38 Hz, oft, 1=10.87 Hz) 5.56 ppm (1H, br s).

Example I(H)

Hexanoic acid, 4-methylamino-4-oxo, (5-methyl-2-(1-methylethyl)cyclohexyl)ester, (1R-(1α,2β,5α))-

Monomenthyl succinate 1 eq, oxalyl chloride 1.3 eq, pyridine 2.6 eq, methylamine (2.0M in THF) 4.0 eq, yield=41% as a waxy off white solid.

0.75 ppm (3H, d, 3=6.96 Hz), 0.85 ppm (1H, m). 0.90 ppm (6H, 2d, J=7.02 and 6.53 Hz), 0.96 ppm (1H, m), 1.04 ppm (1H, m), 1.36 ppm (1H, m), 1.48 ppm (1H, m), 1.66 ppm (6H, m), 1.84 ppm (1H, d, J=2.68 Hz, of quintet or higher, J=6.98 Hz), 1.97 ppm(1H, m), 2.19 ppm (2H, m), 2.31 ppm (2H, m, 1), 2.81 ppm (3H, d, J=4.84 Hz, m), 4.68 ppm (1H, d, J=4.39 Hz, oft, J=10.88 Hz), 5.53 ppm (2H, br s).

Example I(I)

Hexanedioic acid, mono(5-methyl-2-(1-methylethyl) cyclohexyl) ester, (1R-(1α,2β,5α))-

Adipic acid 1 eq, toluene 2 weight equivalents, menthol 1 eq, pTSA (catalyst), extract acid with 10% potassium hydroxide solution, acidify, yield=25% as a waxy solid.

0.75 ppm (3H, d, J=6.97 Hz), 0.85 ppm (1H, m), 0.90 ppm (6H, 2d, J=7.02 and 6.55 Hz), 0.97–1.11 ppm (2H, m), 1.37 ppm (1H, m), 1.49 ppm (1H, m), 1.68 ppm (6H, m), 1.85 ppm (1H, d, J=2.67 Hz, of quintet or higher, J=6.97 Hz), 1.98 ppm (1H, m), 2.35 ppm (4H, 2t, J=7:00 and 7.22 Hz), 4.69 ppm (1H, d, J=4.37 Hz, of t, J=10.87 Hz), 11.23 ppm (1H, br s).

Example I(J)

Octanedioic acid, mono(5-methyl-2-(1-methylethyl) cyclohexyl) ester, (1R-(1α,2β,5α))

Suberic acid 1 eq, toluene 4 weight equivalents, menthol 0.5 eq, pTSA (cat), yield=20% as a syrup.

0.71 ppm (3H, d, J=6.94 Hz), 0.86 ppm (1H, m, and 6H, 2d, J=6.78 and 6.30 Hz), 0.95 ppm (1H, m), 0.96–1.08 ppm (1H, m), 1.25 ppm (4H, m), 1.33 ppm (1H, m), 1.48 ppm (5H, m), 1.63 ppm (2H, m), 1.84 ppm (2H, m), 2.17 ppm (2H, t, J=7.36 Hz), 2.24 ppm (2H, t, J=7.23 Hz), 4.58 ppm (1H, d, J=4.32 Hz, of t, J=10.87 Hz), 10.42 ppm (1H, br s).

Example II

Preparation of a Chewing Gum 100 parts by weight of chicle were mixed with 4 parts by weight of a fruity citrus gum flavor which was a blend of lemon oil, ethyl butyrate, ethyl acetate, benzaldehyde, citral and alpha ionone in equal portions. To the resulting mixture, 300 parts by weight of sucrose and 100 parts by weight of corn syrup were added. Mixing was effected in a ribbon blender with jacketed sidewalls, manufactured by Baker Perkins Co. The resultant chewing gum blend was then manufactured into strips 1 inch in width and 0.1 inches in thickness. These strips were cut into lengths of 3 inches each. This control gum exhibited a fruity lemon flavor without imparting any cooling effect. A second gum sample was prepared using the above recipe with the addition of 1 part by weight of menthyl N,N-dimethyl succinamide, prepared according to Example I(C). The resulting gum had a taste profile substantially identical to the taste profile of the control gum, however the sweetness of the flavor was enhanced and the gum exhibited a pleasant and substantive cooling effect on the tongue and roof of the mouth.

Example III

Preparation of Hard Candy

The following formulation was prepared:

| Ingredients | Parts by Weight |
| --- | --- |
| Sucrose | 137 grams |
| Corn Syrup 42 DE | 91 grams |
| Water | 46 grams |

The above formulation was added to a stainless steel pot. With constant mixing, the formulation temperature was raised to 295° F. The pot was then removed from the heat, and 0.3 grams of cherry flavor containing the ingredients in equal amounts benzaldehyde, tolyl aldehyde, ethyl acetate, maltol, Davana oil and methyl heptinyl carbonate and 1.2 grams of citric acid was added. The resulting liquid candy was then deposited into molds, and the molds containing the liquid candy were cooled to room temperature, yielding 200 grams of finished hard candy. The resulting control candy exhibited a green, candied cherry type of flavor without exhibiting any cooling effect. A second candy sample was prepared using the above recipe modified by the addition of 0.2 grams of menthyl succinamide prepared according to the procedure of Example I (A). This second candy sample exhibited a moderately strong and substantive cooling effect, a very slight bitterness and a flavor profile which was substantially identical to the flavor profile of the control sample.

Cited U.S. Patents and Published Patent Applications Incorporated Herein by Reference All U.S. Patents and Published Patent Applications as set forth are herein incorporated by reference.

What is claimed is:

1. A process for augmenting, enhancing or imparting a taste or cooling effect or refreshing effect to a consumable material selected from the group consisting of a foodstuff, a beverage, a chewing gum, an oral care product, a nasal care product, a cologne, a skin care product, a hair care product, a topical cosmetic product and a medicinal product comprising the step of adding to said consumable material a taste- or cooling effect- or refreshing effect-augmenting, enhancing or imparting quantity and concentration of at least one menthyl half acid ester derivative having the structure:

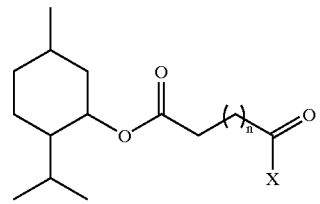

wherein n is an integer of from 1 to 5; wherein X is selected from the group consisting of —OR" and —NRR'; wherein R" is hydrogen, $C_1$–$C_5$ lower alkyl or $C_3$–$C_6$ lower alkenyl; wherein R is hydrogen, $C_1$–$C_5$ lower alkyl, 2-hydroxyethyl or cyclopropyl and wherein R' is hydrogen, methyl or ethyl; with the proviso that when X is —OR", n is an integer of from 3 to 5.

2. The process of claim 1 wherein in the menthyl half acid ester derivative, n is 3 and X is —OH, and the menthyl half acid ester is monomenthyl adipate having the structure:

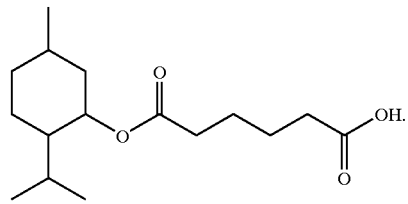

3. The process of claim 1 wherein in the menthyl half acid ester derivative, n is 3 and X is —OH and the menthyl acid ester is the monomenthyl adipate isomer, 1R(1α,2β,5α) monomenthyl adipate having the structure:

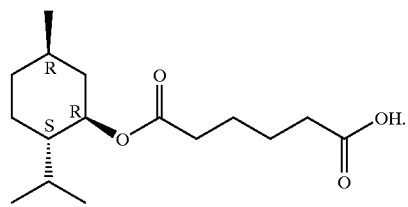

4. The process of claim 1 wherein the menthyl half acid ester derivative has a structure selected from the group consisting of:

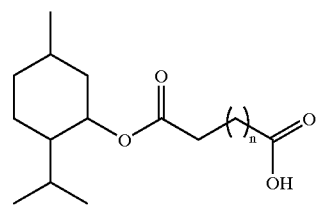

wherein n is an integer of from 3 to 5; and

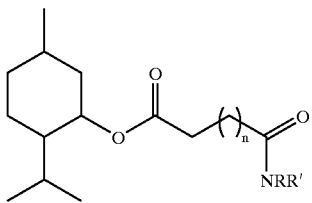

wherein n is an integer of from 1 to 5; wherein R is hydrogen, $C_1$–$C_5$ lower alkyl, 2-hydroxyethyl or cyclopropyl and wherein R' is hydrogen, methyl or ethyl.

5. The process of claim 1 wherein the menthyl half acid ester derivative has a structure selected from the group consisting of:

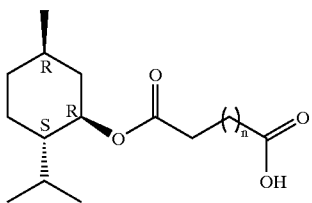

wherein n is an integer of from 3 to 5; and

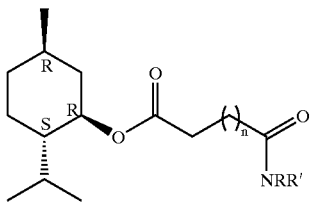

1 to 5; wherein R is hydrogen, $C_1$–$C_5$ lower alkyl) 2-hydroxyethyl or cyclopropyl and wherein R' is hydrogen, methyl or ethyl.

6. A process for producing a menthyl half acid ester derivative having the structure:

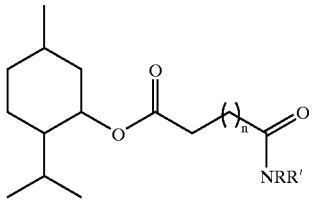

comprising the steps of admixing a compound having the structure:

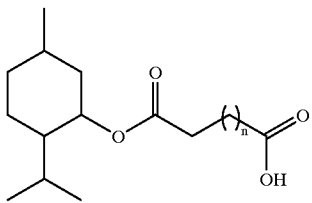

with an inert solvent to form a solution; then admixing the resulting solution with an aliphatic or aromatic tertiary amine base at a temperature in the range of from about 0° C. to about 30° C.; then admixing the resulting product with an oxalyl dihalide while maintaining the reaction temperature in the range of from about 5° C. to about 30° C. thereby forming an intermediate; then admixing the resulting intermediate with an amine having the formula RR'NH at a temperature in the range of from about 0° C. to about 30° C.; and then isolating the compound having the structure:

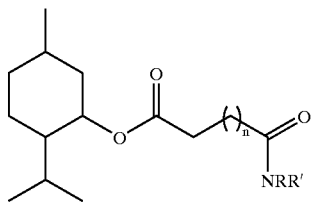

from the resulting product wherein n is an integer of from 1 to 5; wherein R is hydrogen, $C_1$–$C_5$ lower alkyl, 2-hydroxyethyl or cyclopropyl and wherein R' is hydrogen, methyl or ethyl.

7. The process of claim 6 wherein the solvent for the compound having the structure:

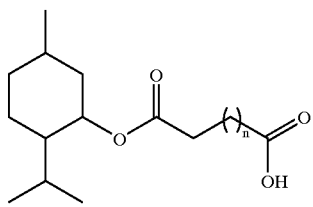

is dichloromethane; the oxalyl dihalide is oxalyl dichloride; the tertiary amine base is pyridine and the process is carried out according to the reaction scheme:

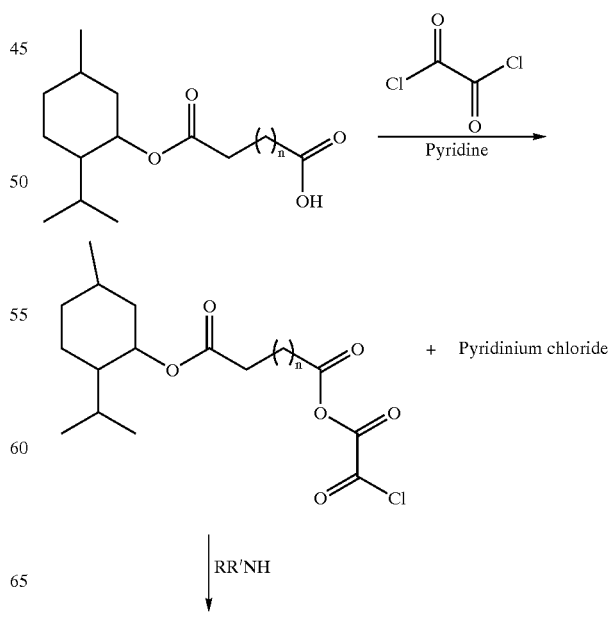

-continued

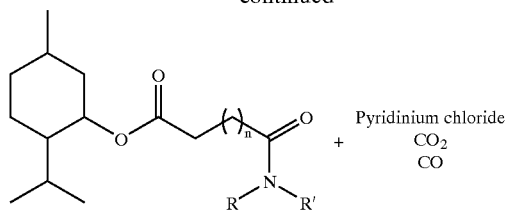 + Pyridinium chloride
$CO_2$
$CO$

8. A process for producing a menthyl half acid ester derivative having the structure:

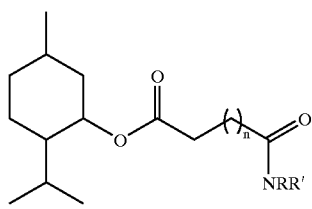

comprising the steps of admixing a compound having the structure:

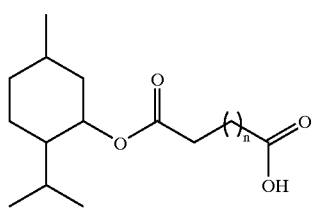

with an inert solvent to form a solution; admixing the resulting solution with a lower alkyl haloformate at a temperature in the range of from about 0° C. up to about 30° C. whereby an intermediate is formed; then cooling the resulting intermediate-containing product to a temperature in the range of from about −30° C. to about +5° C.; then admixing the resulting intermediate-containing product with an aliphatic or aromatic tertiary amine while maintaining the temperature of the mixture at from about −15° C. to about +5° C.; filtering the resulting mixture; cooling the filtrate to a temperature in the range of from about −15° C. to about +5° C.; admixing the resulting product with an amine having the formula RR'NH at a temperature in the range of from about 0° C. to about 30° C.; and then isolating the compound having the structure:

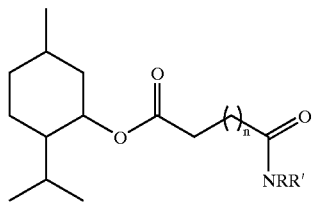

from the resulting reaction product, wherein n is an integer of from 1 up to 5; wherein R is hydrogen, $C_1$–$C_5$ lower alkyl, 2-hydroxyethyl or cyclopropyl and wherein R' is hydrogen, methyl or ethyl.

9. The process of claim 8 wherein the solvent for the compound having the structure:

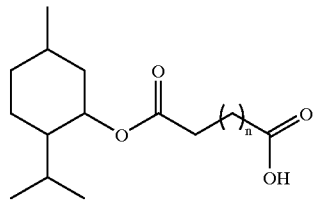

is dichloromethane; the lower alkyl haloformate is ethyl chloroformate; the tertiary amine is tirethylamine and the process is carried out according to the reaction scheme:

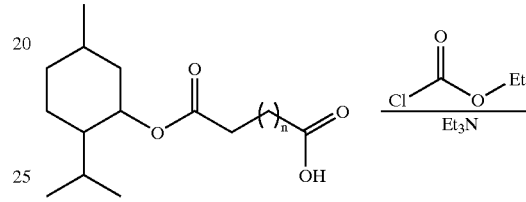

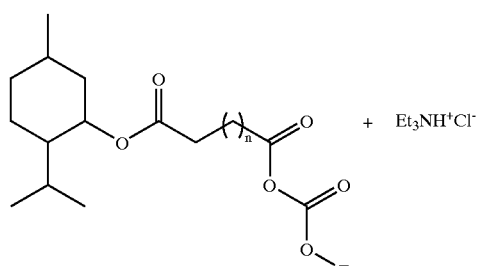 + $Et_3NH^+Cl^-$

↓ RR'NH

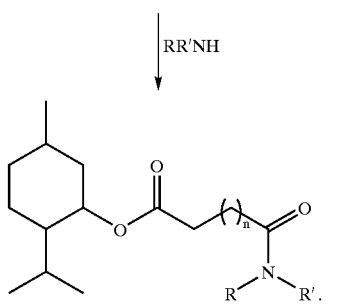

10. A process for producing a menthyl half acid ester derivative having the structure:

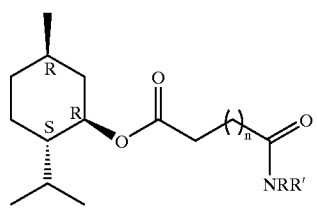

comprising the steps of admixing a compound having the structure:

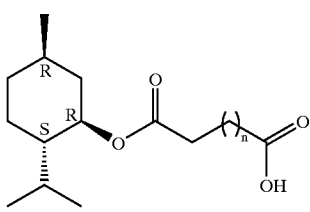

with an inert solvent to form a solution; then admixing the resulting solution with an aliphatic or aromatic tertiary amine base at a temperature in the range of from about 0° C. to about 30° C.; then admixing the resulting product with an oxalyl dihalide, maintaining the reaction temperature in the range of from about 5° C. up to about 30° C. thereby forming an intermediate; then admixing the resulting intermediate with an amine having the formula RR'NH at a temperature in the range of from about 0° C. to about 30° C.; and then isolating the compound having the structure:

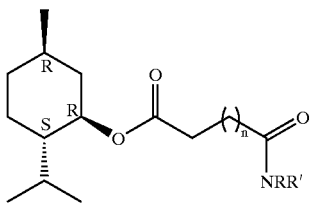

from the resulting reaction product wherein n is an integer of from 1 to 5; wherein R is hydrogen, $C_1$–$C_5$ lower alkyl, 2-hydroxyethyl or cyclopropyl and wherein R' is hydrogen, methyl or ethyl.

11. The process of claim 10 wherein the solvent for the compound having the structure:

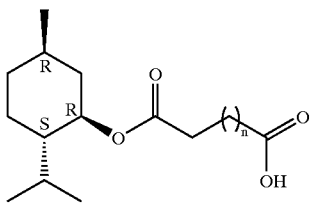

is dichloromethane; the oxalyl dihalide is oxalyl dichloride; the tertiary amine base is pyridine and the process is carried out according to the reaction scheme:

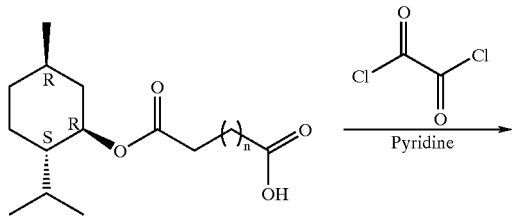

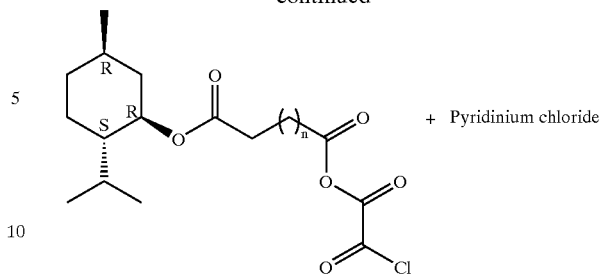

+ Pyridinium chloride

RR'NH

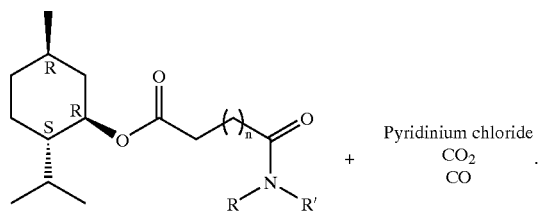

+ Pyridinium chloride
  $CO_2$
  CO

12. A process for producing a menthyl half acid ester having the structure:

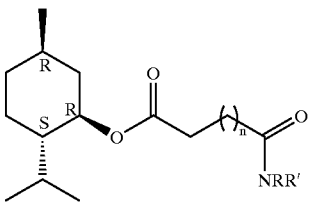

comprising the steps of admixing a compound having the structure:

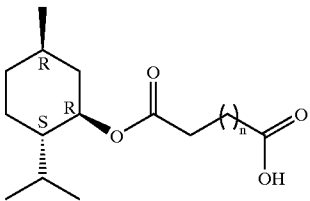

with an inert solvent to form a solution; admixing the resulting solution with a lower alkyl haloformate at a temperature in the range of from about 0° C. to about 30° C. whereby an intermediate is formed; then cooling the resulting intermediate-containing product to a temperature in the range of from about −30° C. to about +5° C.; then admixing the resulting intermediate-containing product with an aliphatic or aromatic tertiary amine while maintaining the temperature of the mixture at from about −15° C. to about +5° C.; filtering the resulting mixture; cooling the filtrate to a temperature in the range of from about −15° C. to about +5° C.; admixing the resulting product with an amine having the formula RR'NH at a temperature in the range of from about 0° C. to about 30° C.; and then isolating the compound having the structure:

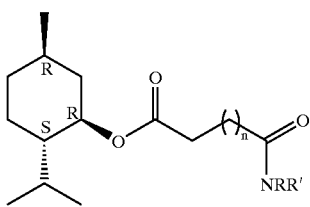

from the resulting reaction product, wherein n is an integer of from 1 to 5; wherein R is hydrogen, $C_1$–$C_5$ lower alkyl, 2-hydroxyethyl or cyclopropyl and wherein R' is hydrogen, methyl or ethyl.

13. The process of claim 12 wherein the solvent for the compound having the structure:

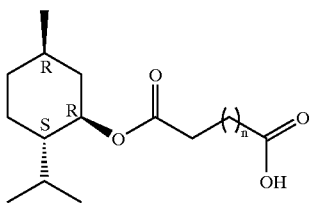

is dichloromethane; the lower alkyl haloformate is ethyl chloroformate; the tertiary amine is triethylamine and the process is carried out according to the reaction scheme:

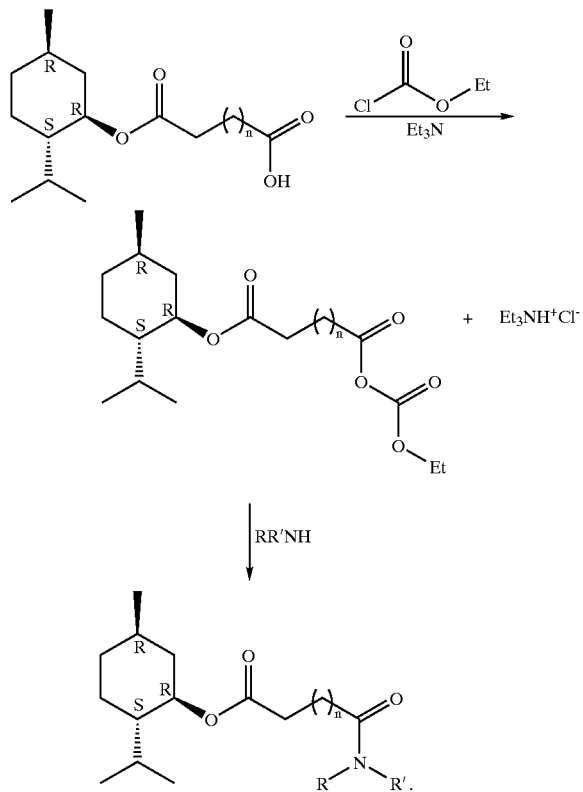

14. The process of claim 1 wherein the consumable material is a chewing gum.

15. The process of claim 1 wherein the consumable material is an oral care product and the oral care product is a toothpaste.

16. The process of claim 1 wherein the consumable material is a foodstuff and the foodstuff is a candy.

17. The process of claim 2 wherein the consumable material is a chewing gum.

18. The process of claim 2 wherein the consumable material is an oral care product and the oral care product is a toothpaste.

19. The process of claim 2 wherein the consumable material is a foodstuff and the foodstuff is a candy.

20. The process of claim 3 wherein the consumable material is a chewing gum.

21. The process of claim 3 wherein the consumable material is an oral care product and the oral care product is a toothpaste.

22. The process of claim 3 wherein the consumable material is a foodstuff and the foodstuff is a candy.

23. The process of claim 4 wherein the consumable material is a chewing gum.

24. The process of claim 4 wherein the consumable material is an oral care product and the oral care product is a toothpaste.

25. The process of claim 4 wherein the consumable material is a foodstuff and the foodstuff is a candy.

26. The process of claim 5 wherein the consumable material is a chewing gum.

27. The process of claim 5 wherein the consumable material is an oral care product and the oral care product is a toothpaste.

28. The process of claim 5 wherein the consumable material is a foodstuff and the foodstuff is a candy.

29. A menthyl half acid ester derivative having the structure:

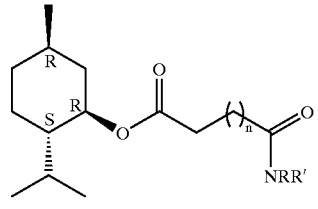

wherein n is an integer of from 1 to 5; wherein R is hydrogen, $C_1$–$C_5$ lower alkyl, 2-hydroxyethyl or cyclopropyl and wherein R' is hydrogen, methyl or ethyl.

30. The menthyl half acid ester derivative of claim 29 wherein R is selected from the group consisting of hydrogen, ethyl and methyl; R' is selected from the group consisting of hydrogen and methyl and n is 1 or 2.

31. The process of claim 1 wherein the menthyl half acid ester derivative has the structure:

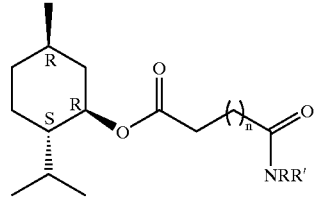

wherein n is an integer of from 1 to 5; wherein R is hydrogen, $C_1$–$C_5$ lower alkyl, 2-hydroxyethyl or cyclopropyl and wherein R' is hydrogen, methyl or ethyl.

32. The process of claim 31 wherein in the menthyl half acid ester derivative having the structure:

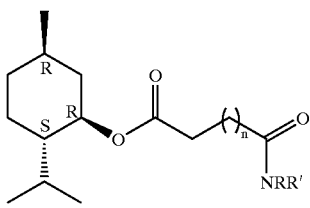

R is selected from the group consisting of hydrogen, ethyl and methyl; R' is selected from the group consisting of hydrogen and methyl and n is 1 or 2.

33. The process of claim 31 wherein the consumable material is a chewing gum.

34. The process of claim 31 wherein the consumable material is an oral care product and the oral care product is a toothpaste.

35. The process of claim 31 wherein the consumable material is a foodstuff and the foodstuff is a candy.

36. The process of claim 32 wherein the consumable material is a chewing gum.

37. The process of claim 32 wherein the consumable material is an oral care product and the oral care product is a toothpaste.

38. The process of claim 32 wherein the consumable material is a foodstuff and the foodstuff is a candy.

* * * * *